United States Patent [19]

Makryaleas et al.

[11] Patent Number: 4,980,284

[45] Date of Patent: Dec. 25, 1990

[54] METHOD OF PREPARING D-ALPHA-AMINO ACIDS

[75] Inventors: Kyriakos Makryaleas, Freig ericht; Karlheinz Drauz, Freigericht, both of Fed. Rep. of Germany

[73] Assignee: Degussa AG, Frankfurt am Main, Fed. Rep. of Germany

[21] Appl. No.: 528,755

[22] Filed: May 25, 1990

[30] Foreign Application Priority Data

Jun. 2, 1989 [DE] Fed. Rep. of Germany ....... 3918057

[51] Int. Cl.$^5$ ............................................. C12P 13/04
[52] U.S. Cl. ....................................... 435/106; 435/43; 435/107; 435/108; 435/114; 435/115; 435/116; 435/245; 435/822
[58] Field of Search ................. 435/106, 244, 245, 43, 435/822, 107, 115, 114, 116, 108

[56] References Cited

U.S. PATENT DOCUMENTS

| | | | |
|---|---|---|---|
| 4,211,840 | 7/1980 | Nakamori et al. | 435/115 |
| 4,237,227 | 12/1980 | Yamada et al. | 435/106 |
| 4,242,452 | 12/1980 | Yamada et al. | 435/106 |
| 4,248,967 | 2/1981 | Viglia et al. | 435/106 |
| 4,312,948 | 1/1982 | Olivieri et al. | 435/106 |
| 4,613,691 | 9/1986 | Mirviss et al. | 562/443 |

FOREIGN PATENT DOCUMENTS 0309310  3/1989  European Pat. Off. ............ 435/106

OTHER PUBLICATIONS

Biotech & Bioeng, vol. 23(10) pp. 2173–2183 (1981) Bibiau CA 96–4917(1) Olivieri et al.

*Primary Examiner*—Herbert J. Lilling
*Attorney, Agent, or Firm*—Cushman, Darby & Cushman

[57] ABSTRACT

A substantial elevation of the space-time yield is achieved in the preparation of D-α-amino acids by means of the biotransformation of hydantoins which are monosubstituted in the 5-position in an aqueous medium in the presence of cells of the microorganism Agrobacterium radiobacter if the biotransformation is carried out under a elevated pressure at the start of the reaction. A further improvement results if this elevated pressure is maintained for a period of at least 16 hours, then removed and the biotransformation continued at atmospheric pressure.

12 Claims, No Drawings

METHOD OF PREPARING D-ALPHA-AMINO ACIDS

The present invention relates to a method of preparing D-α-amino acids by means of the biotransformation of hydantoins which are monosubstituted in the 5-position. The process is carried out in an aqueous medium with a pH of at least 6.5 in the presence of cells of the microorganism Agrobacterium radiobacter.

BACKGROUND OF THE INVENTION

D-α-amino acids are valuable intermediates for the preparation of pharmaceutically-active substances (e.g. D-phenyl glycine and D-4-hydroxyphenyl glycine for the synthesis of penicillins and cephalosporins) or pesticides (e.g. D-valine for the synthesis of the insecticide fluvalinate. D-alanine is used in the preparation of the dietetic sweetening agent Alitam ®.omega ureidoalkyl-D-α-amino acids and omega-ureidoheteroalkyl-D-α-amino acids are analogs of D-citrulline. D-citrulline and D-homocitrulline are used in potent LH-RH antagonists and are therefore valuable compounds.

"Biotechnology and Bioengineering", vol. XXIII, pp. 2173–2183, (1981) teaches the preparation of various D-α-amino acids by means of the biotransformation of hydantoins appropriately substituted in the 5-position. The process is carried out in an aqueous medium with a pH of at least 6.5 in the presence of cells of the microorganism Agrobacterium radiobacter. The biotransformation is carried at atmospheric pressure. The total yield is only 60% in the case of D-4-hydroxyphenyl glycine.

SUMMARY OF THE INVENTION

The object of the present invention is to improve the yield in the preparation of D-α-amino acids by means of the biotransformation of hydantoins which are monosubstituted in the 5-position. As heretofore, the method of the present invention is carried out in an aqueous medium with a pH of at least 6.5 in the presence of cells of the microorganism Agrobacterium radiobacter. However, in the method of the present invention, the biotransformation is carried out in a closed reactor, a pressure between 1 bar and 30 bars is established in the reactor at the start of the reaction and this pressure is maintained for a period of at least 16 hours. This causes a considerable increase in space-time yield.

A further considerable increase of the space-time yield surprisingly results when the elevated pressure is released from the reactor after the reaction is partially completed.

It is especially advantageous to maintain the elevated pressure for a period of 16 to 30 hours, preferably from 20 to 25 hours, then to remove the pressure and to carry out the biotransformation for a further period of 18 to 32 hours, preferably from 23 to 28 hours, at atmospheric pressure.

The elevated pressure is advantageously produced by means of on an inert gas, preferably nitrogen. It is maintained for a period of 16 to 30 hours, preferably 20 to 25 hours. A pressure between 2 and 10 bars is preferred.

A plurality of hydantoins monosubstituted in the 5-position can be transformed by method of the invention into the corresponding D-α-amino acids. Possible substituents in the 5-position are e.g. straight-chain, branched or cyclic alkyl groups with 1 to 12 carbon atoms such as methyl, ethyl, n-propyl, isopropyl, isobutyl, 1-methylpropyl, tert. butyl, cyclopentyl or cyclohexyl groups; straight-chain, branched or cyclic unsaturated hydrocarbon groups such as 2-propenyl, 2-butenyl, 1-cyclohexenyl or 1,4- cyclohexadienyl groups; hydrocarbon groups of the type mentioned which are monosubstituted or polysubstituted by hydroxyl, carboxyl, sulfhydryl, alkylmercapto, amino, alkylamino, alkoxy, carbamoyl, guanidino, ureido, ureidoalkyl-oxyalkyl, ureidoalkyl-mercaptoalkyl, ureidoalkyl-aminoalkyl, sulfoxyl, nitro, halogen, acyl, aminosulfenyl, arylmercapto, 4-imidazolyl or 4-thienyl groups; aromatic hydrocarbon groups such as phenyl or naphthyl groups which are optionally monosubstituted or polysubstituted by alkyl, alkenyl, cyclic alkyl or alkenyl, hydroxyl, alkoxyl, halogen, benzyloxy, benzyloxymethyloxy, methoxymethyloxy, acyloxy, acyl, aryloxy, amino, acylamino, alkylamino, nitro, carboxyl and carbamoyl groups; heteroaromatic groups such as 2-thienyl, 5-thiazolyl, 4-imidazolyl or 2-furyl groups which are optionally monosubstituted or polysubstituted by the groups already mentioned above, aralkyl or heteroarylalkyl groups which are optionally monosubstituted or polysubstituted by the groups already mentioned above.

The hydantoins monosubstituted in the 5-position can be prepared e.g. by means of Strecker synthesis from the corresponding aldehydes, hydrocyanic acid and ammonia/carbon dioxide or ammonium carbonate. If the corresponding aldehydes are not available, the hydantoins can also be prepared as an alternative from the corresponding α-amino acids in a known manner by means of reacting them with potassium cyanate and a subsequent treatment of the N-carbamoyl-α-amino acids formed at first with an acid. The α-amino acids can be added both in the L as well as also in the D,L form or as partial racemates.

The method of the invention is generally carried out in an aqueous medium with a pH between 6.5 and 11.0, preferably between 7.0 and 9.0. The preferred temperature is between 20°C. and 60°C., especially between 35°C. and 45°C.

The initial concentration of the hydantoins monosubstituted in the 5-position should generally be 5% to 30% by weight. Due to the frequently poor solubility of the hydantoins, they are often present at first in suspended form. However, this is not a problem for the biotransformation because the substrate is constantly replaced, as it is consumed, by newly dissolved substrate.

As a consequence of the D-stereospecificity of the enzymes active in the microorganism Agrobacterium radiobacter, basically only the D-enantiomers of the hydantoins are reacted. However, since the hydantoins racemize spontaneously under the reaction conditions, the L-enantiomers are also converted totally into the corresponding D-α-amino acids.

The amount of biocatalyst (cells) to be added is a function of the affinity of the particular substrate for the active enzymes. In general, an amount which provides a weight ratio between 1:4 and 1:40 relative to the hydantoin added is advantageous.

The D-α-amino acids prepared in accordance with the method of the invention can be isolated in a simple manner, e.g. by means of ion exchangers or by precipitation at the isoelectric point.

The following examples and comparative examples are intended to illustrate the method of the invention in more detail. The determination of the conversion takes place in each instance by means of the quantitative determination of the D-α-amino acid produced by means of high-performance liquid chromatography.

EXAMPLE 1

A suspension of 60 g D,L isopropylhydantoin in 716.7 g $H_2O$ with a pH of 8.4 was transferred into a 1 l Buchi laboratory autoclave and the autoclave was charged with $N_2$ for approximately 10 minutes at 40°C. Then, 83.3 g biomass suspension were added into the reactor. The suspension was slightly agitated and charged for a further 10 minutes with $N_2$.

Thereafter, the reactor was sealed and an elevated pressure of 1.0 bar established with $N_2$. The reaction took place at 40°C. with slight agitation. After 21 hours the pressure was released from the reactor and after a further 27 hours at 40°C. the reaction was ended. The final conversion was 95 % of theory.

After separation of the biomass with an ultrafiltration membrane, the pH of the solution was adjusted to 6.0, the solution was concentrated by evaporation on a rotary evaporator and cooled while combining with methanol. With 43.0 g isolated D-valine, the yield of the recovered product was 87%, relative to the D,L isopropylhydantoin added. The isolated product had the following characteristics:
   Content (HPLC) : 100% (only 1 peak).
   Specific rotation : $[\alpha]D^{20} = -28.0°$ (c=8 in 6N HCl).
   D,L distribution : D-Val=99.83; L-Val=0.17%.

REFERENCE EXAMPLE 1

Example 1 was repeated except that the pressure during the first part of the reaction was atmospheric pressure. After 48 hours the conversion was only 60% of theory.

EXAMPLE 2

Example 1 was repeated except that the pressure was not reduced in the reactor after 21 hours but rather maintained for 48 hours. The final conversion was 85% of theory.

EXAMPLE 3

The same procedure was used as in Example 1; however, 60 g D,L-methylhydantoin were used and the pressure during the first part of the reaction was 3.8 bars. The final conversion was 93% of theory and the yield of D-alanine which was isolated was 84%, relative to the D,L-methylhydantoin used. The isolated product had the following characteristics:
   Content (HPLC) : 100% (only 1 peak).
   Specific rotation : $[\alpha]D^{20} = -14.2°$ (c=10 in 6N HCl).

REFERENCE EXAMPLE 2

Example 3 was repeated except that reaction was carried out at atmospheric pressure. After 48 hours the conversion was only 56% of theory.

EXAMPLE 4

The same process was used as in Example 1; however, 60 g D,L phenylhydantoin and 41.6 g biomass suspension were added and the pressure during the first part of the reaction was 6.0 bars. After 48 hours the final conversion was over 98% of theory. The isolated D-phenylglycine had the following characteristics:
   Content (HPLC) : 100% (only 1 peak).
   Specific rotation : $[\alpha]D^{20} = -155.3°$ (c=1 in 1N HCl).

REFERENCE EXAMPLE 4

Example 4 was repeated except that the reaction was carried out at atmospheric pressure. After 48 hours the conversion was only 59% of theory.

EXAMPLE 5

The same process was used as in Example 1; however, 60 g 5-(4-hydroxyphenyl)-hydantoin were added and the pressure during the first part of the reaction was 6.0 bars. After 20 hours at elevated pressure the final conversion was 100% of theory. The isolated D-(4-hydroxyphenyl)-glycine had the following characteristics:
   Content (HPLC) : 100% (only 1 peak).
   Specific rotation : $[\alpha]D^{20} = -158.4°$ (c=1 in 1N HCl).

REFERENCE EXAMPLE 5

Example 5 was repeated except that the process was carried out at atmospheric pressure. After 20 hours the conversion was only 63% of theory.

EXAMPLE 6

The same process was used as in Example 1; however, 60 g D,L-pyridylmethylhydantoin were added and the pressure during the first part of the reaction was 6.0 bars. After 48 hours the final conversion was 100% of theory. The yield of 3-(2-pyridyl)-D-alanine isolated was 93% of theory. The isolated product had the following characteristics:
   Content (HPLC) : 100% (only 1 peak).
   Specific rotation : $[\alpha]D^{20} = -26.21°$ (c=1 in 2N HCl)
   D,L distribution : D=100%; L=0%.

EXAMPLE 7

The same process was used as in Example 1; however, 60 g D,L-naphthylmethylhydantoin were added and the reaction pressure during the first part of the reaction was 6.0 bars. After 48 hours the final conversion was 92% of theory. The isolated product had the following characteristics:
   Content (HPLC) : 100% (only 1 peak).
   Specific rotation : $[\alpha]D^{20} = +2.6°$ (c=2 in 2N NaOH).
   D,L distribution : D=99.4%; L=0.6%.

EXAMPLE 8

The same process was used as in Example 1; however, 60 g L-citrulline hydantoin were added and the pressure during the first part of the reaction was 6.0 bars. After 48 hours the final conversion was 100% of theory and the yield of D-citrulline isolated was 92%, relative to the hydantoin added. The isolated product had the following characteristics:
   Content (HPLC) : 100% (only 1 peak).
   Specific rotation : $[\alpha]D^{20} = +24.0°$ (c=2 in 1N HCl).

EXAMPLE 9

The same process was used as in Example 1; however, 60 g D,L-5-methylmercaptoethylhydantoin were added and the pressure during the first part of the reaction was 1.6 bars. After 48 hours the final conversion was 94% of theory. The isolated product had the following characteristics:
   Content (HPLC) : 100% (only 1 peak).
   Specific rotation : $[\alpha]D^{20} = -23.9°$ (c=5 in 5N HCl).

EXAMPLE 10

The same process was used as in Example 1; however, 60 g L-5-(1-hydroxyethyl)-hydantoin (2 S, 3 R) were added and the pressure during the first part of the reaction was 3.8 bars. After 48 hours the final conversion was 90% of theory. The isolated D-allothreonine (2 R, 3 R) had the following characteristics:

Content (HPLC) : 100% (only 1 peak).
Specific rotation : $[\alpha]D^{20} = -32.5°$ (c=1 in 1 N HCl).

EXAMPLE 11

The same process was used as in Example 1; however, 60 g D,L-5-(3-indolylmethyl)-hydantoin were added and the pressure during the first part of the reaction was 2.5 bars. After 48 hours the final conversion was 87% of theory. The isolated D-tryptophane had the following characteristics:

Content (HPLC) : 100% (only 1 peak).
Specific rotation : $[\alpha]D^{20} = +32.1°$ (c=1 in $H_2O$).

EXAMPLE 12

The same process was used as in Example 1; however, 60 g L-5-(4-hydroxybenzyl)-hydantoin were added and the pressure during the first part of the reaction was 1.8 bars. After 48 hours the final conversion was 89% of theory. The isolated D-tyrosine had the following characteristics:

Content (HPLC) : 100% (only 1 peak).
Specific rotation : $[\alpha]D^{20} = +11.4°$ (c=4 in 1 N HCl).

EXAMPLE 13

The same process was used as in Example 1; however, 60 g L-5-(4-imidazoylmethyl)-hydantoin were added and the pressure during the first part of the reaction was 1.5 bars. After 48 hours the final conversion was 86% of theory. The isolated D-histidine had the following characteristics:

Content (HPLC) : 100% (only 1 peak).
Specific rotation : $[\alpha]D^{20} = +39.6°$ (c=5 in $H_2O$).

EXAMPLE 14

The same process was used as in Example 1; however, 60 g 5-(2-ureidoethyl)-D,L-hydantoin were added an the pressure during the first part of the reaction was 3 bars. After 48 hours the final conversion was 95% and the isolated yield after purification on a sharply acidic ion exchanger was 80% of theory. The isolated 3-(ureido-methyl)-D-alanine (D-norcitrulline) had the following characteristics:

Content (HPLC) : 100% (only 1 peak).
Melting point : 200–201°C.
Specific rotation : $[\alpha]D^{20} = -22.4°$ (c=1 in 0.5N HCl).

EXAMPLE 15

The same process was used as in Example 1; however, 60 g 5-(ureidomethyl)-D,L-hydantoin were added and the pressure during the first part of the reaction was 3 bars. After 48 hours the final conversion was 90% of theory and the isolated yield after purification on a sharply acidic ion exchanger was 80% of theory. The isolated 3-ureido-D-alanine had the following characteristics:

Content (HPLC) : 100% (only 1 peak).
Melting point : 203–203.5°C.
Specific rotation : $[\alpha]D^{20} = +66.8°$(c=1 in $H_2O$).

EXAMPLE 16

The same process was used as in Example 1; however, 60 g 5-(2-ureidoethyl-thiomethyl)-L-hydantoin hydrochloride were added and the pressure during the first part of the reaction was 3.2 bars. After 48 hours the final conversion was 100% and the isolated yield after purification on a sharplyacidic ion exchanger 85% of theory. The isolated S-(2-ureidoethyl)-D cysteine had the following characteristics:

Content (HPLC) : 100% (only 1 peak).
Melting point : 192.5–193.5°C. (decomposition).
Specific rotation : $[\alpha]D^{20} = +15.3°$(c=1 in $H_2O$).

EXAMPLE 17

The same process was used as in Example 1; however, 60 g 5-(2-ureidoethyl-oxymethyl)-D,L-hydantoin were added and the pressure during the first part of the reaction was 3.2 bars. After 48 hours the final conversion was 100%. The isolated 0-(2-ureidoethyl)-D-serine had the following characteristics:

Content (HPLC) : 100% only 1 peak).
NMR ($D_2O$) : 3.86–4.0 (m, 3H); 3.52–3.7 (m, 2H); 3.22–3.38 (m, 2H) ppm.
$R_f$ value DC : 0.27 (ethanol/25% $NH_3$ solution=8:2).

EXAMPLE 18

The same process was used as in Example 1; however, 60 g 5-(2-ureidoethyl-thioethyl)-D,L-hydantoin hydrochloride were added and the pressure during the first part of the reaction was 3.2 bars. After 48 hours the final conversion was 100% and the isolated yield after purification on a sharply acidic ion exchanger 85% of theory. The isolated S-(2-ureidoethyl)-D-homocysteine had the following characteristics:

Content (HPLC) : 100% (only 1 peak).
Melting point : 208.5–209°C. (decomposition).
Specific rotation : $[\alpha]D^{20} = +6.75°$ (c=1 in $H_2O$).

EXAMPLE 19

The same process was used as in Example 1; however, 60 g 5-(2-ureidoethyl-thioisopropyl)-D,L-hydantoin were added and the pressure during the first part of the reaction was 3.2 bars. After 48 hours the final conversion was 80% and the isolated yield of S-(2-ureidoethyl)-D-penicillamine 65% of theory after purification on a sharply acidic ion exchanger.

EXAMPLE 20

The same process was used as in Example 1; however, 60 g 5-(2-thienyl)-D,L-hydantoin were added and the pressure was 1.6 bars. After 19 hours under elevated pressure the final conversion was 100% of theory. The isolated 2-thienyl-D-glycine exhibited the following analytic values:

Content (HPLC) : 100% (only 1 peak).
Melting point : 206–209°C.
Specific rotation : $[\alpha]D^{20} = -108.5°$ (c=1 in 1N HCl).

EXAMPLE 21

The same process was used as in Example 1; however, 60 g 5-(1-mercapto-1-methyl-ethyl)-D,L-hydantoin were added and the pressure during the first part of the reaction was 3.5 bars. After 48 hours the final conversion was 65% of theory. The isolated D-penicillamine exhibited the following analytic values:

Content (HPLC) : 100% (only 1 peak).

Specific rotation : $[\alpha]D^{20} = -63.0°$ (c=1 in pyridine).
D,L distribution : D=99.9%, L=0.1%.

COMPARATIVE EXAMPLE 21

Example 21 was repeated except the reaction was carried out at atmospheric pressure. After 48 hours the conversion was less than 10% of theory.

What is claimed is:

1. In a method of preparing D-α-amino acids by biotransformation of hydantoins which are monosubstituted in the 5-position in an aqueous medium at a pH of at least 6.5 in the presence of cells of the microorganism Agrobacterium radiobacter;

the improvement which comprises carrying out the biotransformation in a closed reactor at an elevated pressure between 1 bar and 30 bars above atmospheric pressure at the start of the reaction and maintaining this pressure for a period of at least 16 hours.

2. A method as set forth in claim 1 in which the pressure of 1 to 30 bars is maintained for a period of 16 to 30 hours, the pressure is then reduced to atmospheric pressure, and the biotransformation is continued for a further period of 18 to 32 hours at atmospheric pressure.

3. A method as set forth in claim 2 in which the elevated pressure is maintained for a period of 20 to 25 hours and the biotransformation is carried out for a further period of 23 to 28 hours at atmospheric pressure.

4. A method as set forth in any one of claims 1, 2 and 3 in which the elevated pressure is established by introduction of an inert gas.

5. A process as set forth in any one of claims 1, 2 and 3 in which the elevated pressure is between 2 and 10 bars above atmospheric pressure.

6. A method as set forth in any one of claims 1, 2 and 3 in which the pH is between 6.5 and 11.0.

7. A method as set forth in claim 6 in which the pH is between 7.0 and 9.0.

8. A method as set forth in any one of claims 1, 2 and 3 in which the temperature is between 20°C. and 60°C.

9. A method as set forth in claim 8 in which the temperature is between 35°C. and 45°C.

10. A method as set forth in any one of claims 1, 2 and 3 in which the initial concentration of the hydantoin monosubstituted in the 5-position is 5% to 30% by weight.

11. A method as set forth in any one of claims 1, 2 and 3 in which the hydantoin which is monosubstituted in the 5-position is partially dissolved, the remainder being suspended initially.

12. A method as set forth in any one of claims 1, 2 and 3 in which the amount of cells of the microorganism Agrobacterium radiobacter is sufficient to provide a weight ratio between 1:4 and 1:40 relative to the hydantoin.

* * * * *